(12) United States Patent
Seo et al.

(10) Patent No.: US 12,385,836 B2
(45) Date of Patent: Aug. 12, 2025

(54) APPARATUS FOR PCR DIAGNOSIS FOR NORMALIZING LIGHT SOURCE POWER AND FLUORESCENCE POWER AND OPERATING METHOD THEREOF

(71) Applicant: Electronics and Telecommunications Research Institute, Daejeon (KR)

(72) Inventors: Hong-Seok Seo, Daejeon (KR); Dong Hoon Song, Daejeon (KR); Jeong Won Park, Daejeon (KR); Chul Huh, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 206 days.

(21) Appl. No.: 18/366,429

(22) Filed: Aug. 7, 2023

(65) Prior Publication Data
US 2024/0060896 A1 Feb. 22, 2024

(30) Foreign Application Priority Data

Aug. 17, 2022 (KR) .................. 10-2022-0102643
Dec. 22, 2022 (KR) .................. 10-2022-0182021

(51) Int. Cl.
*G01N 21/64* (2006.01)
*C12Q 1/686* (2018.01)

(52) U.S. Cl.
CPC .......... *G01N 21/645* (2013.01); *C12Q 1/686* (2013.01); *G01N 21/6428* (2013.01); *C12Q 2563/107* (2013.01); *G01N 2021/6432* (2013.01); *G01N 2021/6441* (2013.01); *G01N 2021/6471* (2013.01); *G01N 2021/6484* (2013.01); *G01N 2201/06146* (2013.01)

(58) Field of Classification Search
CPC ............ G01N 21/645; G01N 21/6428; G01N 2021/6432; G01N 2021/6441; G01N 2021/6471; G01N 2021/6484; G01N 2201/06146; G01N 21/6452; G01N 2021/6419; C12Q 1/686; C12Q 2563/107
See application file for complete search history.

(56) References Cited

U.S. PATENT DOCUMENTS

| 8,137,616 | B2 | 3/2012 | Sagner et al. | |
| 10,330,684 | B1* | 6/2019 | Campton | ............ G01N 33/582 |
| 2010/0216656 | A1* | 8/2010 | Lockhart | ............ C12Q 1/6837 506/9 |

(Continued)

FOREIGN PATENT DOCUMENTS

| KR | 10-2012-0025034 | 3/2012 |
| KR | 10-2022-0026993 | 3/2022 |

OTHER PUBLICATIONS

Fotso Gueutue et al., "Nanosecond time-resolved Raman spectroscopy for solving some Raman problems such as luminescence or thermal emission", Journal of Raman Spectroscopy, Jan. 16, 2018, pp. 822-829, vol. 49.

*Primary Examiner* — David P Porta
*Assistant Examiner* — Mamadou Faye
(74) *Attorney, Agent, or Firm* — KILE PARK REED & HOUTTEMAN PLLC

(57) ABSTRACT

An apparatus for polymerase chain reaction (PCR) diagnosis for normalizing light source power and fluorescence power and an operating method thereof are disclosed.

20 Claims, 7 Drawing Sheets

(56) References Cited

U.S. PATENT DOCUMENTS

| | | | |
|---|---|---|---|
| 2010/0324834 A1* | 12/2010 | Treptow | G01N 21/6452 702/32 |
| 2015/0322488 A1* | 11/2015 | Gambini | G01N 21/6452 435/287.2 |
| 2022/0228984 A1 | 7/2022 | Kim | |
| 2022/0288594 A1 | 9/2022 | Kim | |

* cited by examiner

CODE1 : 1, 0, 0, 1, 0, 1, 1, 0, 0, 1, 1, 0, 1, 0, 0, 1
CODE2 : 0, 1, 1, 0, 1, 0, 0, 1, 0, 1, 1, 0, 1, 0, 0, 1
CODE3 : 0, 1, 0, 1, 0, 1, 0, 1, 0, 1, 0, 1, 0, 1, 0, 1
CODE4 : 0, 0, 1, 1, 0, 0, 1, 1, 0, 0, 1, 1, 0, 0, 1, 1
CODE5 : 1, 1, 0, 0, 1, 1, 0, 0, 0, 0, 1, 1, 0, 0, 1, 1
CODE6 : 1, 0, 1, 0, 0, 1, 0, 1, 1, 0, 1, 0, 0, 1, 0, 1

| CODE1 | 1 | 0 | 0 | 1 | 0 | 1 | 1 | 0 | 0 | 1 | 1 | 0 | 1 | 0 | 0 | 1 |
|---|---|---|---|---|---|---|---|---|---|---|---|---|---|---|---|---|
| DS1 | $a_1$ | $a_2$ | $a_3$ | $a_4$ | $a_5$ | $a_6$ | $a_7$ | $a_8$ | $a_9$ | $a_{10}$ | $a_{11}$ | $a_{12}$ | $a_{13}$ | $a_{14}$ | $a_{15}$ | $a_{16}$ |

| CODE1 | 1 | -1 | -1 | 1 | -1 | 1 | 1 | -1 | -1 | 1 | 1 | -1 | 1 | -1 | -1 | 1 |
|---|---|---|---|---|---|---|---|---|---|---|---|---|---|---|---|---|
| DS1 | $a_1$ | $a_2$ | $a_3$ | $a_4$ | $a_5$ | $a_6$ | $a_7$ | $a_8$ | $a_9$ | $a_{10}$ | $a_{11}$ | $a_{12}$ | $a_{13}$ | $a_{14}$ | $a_{15}$ | $a_{16}$ |

$$CODE1 \cdot DS1 = 1*a_1 + (-1)*a_2 + (-1)*a_3 + 1*a_4 + (-1)*a_5 + 1*a_6 + 1*a_7 + (-1)*a_8 + (-1)*a_9$$
$$+ 1*a_{10} + 1*a_{11} + (-1)*a_{12} + 1*a_{13} + (-1)*a_{14} + (-1)*a_{15} + 1*a_{16}$$

APPARATUS FOR PCR DIAGNOSIS FOR NORMALIZING LIGHT SOURCE POWER AND FLUORESCENCE POWER AND OPERATING METHOD THEREOF

CROSS-REFERENCE TO RELATED APPLICATION

This application claims the benefit of Korean Patent Application No. 10-2022-0102643 filed on Aug. 17, 2022, and Korean Patent Application No. 10-2022-0182021 filed on Dec. 22, 2022, in the Korean Intellectual Property Office, the entire disclosure of which is incorporated herein by reference for all purposes.

BACKGROUND

1. Field of the Invention

One or more embodiments relate to an apparatus for polymerase chain reaction (PCR) diagnosis for normalizing light source power and fluorescence power, and an operating method thereof.

2. Description of the Related Art

A molecular diagnosis technology is a technology for analyzing molecules that cause diseases in the body, such as diseases caused by viruses or other genetic diseases. The molecular diagnosis technology may allow highly accurate analysis of whether disease-causing deoxyribonucleic acid (DNA) is contained through the amplification of DNA. The molecular diagnosis technology includes preprocessing a bio-sample to be measured, extracting DNA, and replicating and amplifying a desired part of the extracted DNA using a polymerase chain reaction (PCR). A phosphor (e.g., SYBR green) is attached to the amplified DNA and an intensity of a fluorescence signal emitted by an optical method is measured. When there is emission of fluorescence corresponding to the attached phosphor, it is determined that the sample contains disease-causing DNA.

The more DNA is amplified, the more phosphors may be attached, and the intensity of fluorescence may increase. In a case of a general PCR, the amplification process proceeds in 30 cycles, and $2^{30}$ DNA chains are replicated. When a PCR of the related art is used, it takes about 4 hours to prepare a bio-sample and proceed with 30 cycles of amplification. In addition, it is also possible to detect multiple DNAs in one sample at once. For this purpose, it is common to configure two or more phosphors and use multi-wavelength light sources. The multi-wavelength light source used in the PCR of the related art is continuous light (white light).

However, when continuous light is used to detect a plurality of DNAs at once, there is a problem in that signals generated from multiple phosphors as well as signals generated from phosphors not attached to DNA chains are mixed to generate noise. In addition, there is a problem in that fluorescence intensity of continuous light of the phosphor decreases over time (photo bleaching). Therefore, there is a need for a technology capable of accurately and efficiently detecting a signal generated from a phosphor while minimizing a PCR amplification cycle.

SUMMARY

Embodiments provide an apparatus and method for polymerase chain reaction (PCR) diagnosis with improved accuracy by normalizing light source power and fluorescence power applied to a plurality of DNA cells included in a PCR chip.

According to an aspect, there is provided an apparatus for polymerase chain reaction (PCR) diagnosis, the apparatus including a transmitter including a multi-wavelength light source for outputting a plurality of light source signals, and configured to apply the plurality of light source signals to a side surface or a rear surface of a PCR chip including a plurality of deoxyribonucleic acid (DNA) cells using the multi-wavelength light source, wherein each of the plurality of DNA cells includes a plurality of DNAs, a code generator configured to generate a plurality of code signals corresponding to the plurality of light source signals, respectively, wherein the plurality of code signals is a Walsh code, and a receiver configured to receive light source reflection data including a plurality of light source reflection signals reflected from each of the DNA cells, to which the plurality of light source signals is applied, obtain light source power for each of the plurality of code signals for each of the DNA cells based on the light source reflection data, receive fluorescence data including a plurality of fluorescence signals received from a phosphor attached to each of the plurality of DNAs, to which the plurality of light source signals is applied, obtain fluorescence power for each of the plurality of code signals for each of the DNA cells based on the fluorescence data, and normalize the light source power and the fluorescence power for each of the DNA cells.

The light source power may be obtained for each of the plurality of code signals for each of the DNA cells by a dot product of the plurality of code signals and the light source reflection data including the plurality of light source reflection signals reflected from each of the DNA cells in response to the light source signal from each of the DNA cells, to which the plurality of light source signals is applied.

The fluorescence power may be obtained for each of the plurality of code signals for each of the DNA cells by a dot product of the plurality of code signals and the fluorescence data including the plurality of fluorescence signals emitted from a phosphor attached to each of the plurality of DNAs, to which the plurality of light source signals is applied.

The receiver may be configured to normalize the light source power and the fluorescence power for each of the plurality of code signals for each of the DNA cells by a ratio of the fluorescence power to the light source power.

The receiver may include a camera configured to receive the light source reflection data and the fluorescence data, and the camera may be configured to receive the light source reflection data and the fluorescence data through two optical fibers connected to the receiver.

The receiver may include a first filter configured to, for one of the two optical fibers, block the light source reflection data and pass the fluorescence data, and a second filter configured to, for the other one of the two optical fibers, attenuate an intensity of the light source reflection data.

One of the two optical fibers may have an end connected to the receiver, where a first filter configured to block the light source reflection data and pass the fluorescence data is coated, and the other one of the two optical fibers may have an end connected to the receiver, where a second filter configured to attenuate an intensity of the light source reflection data is coated.

According to another aspect, there is provided an apparatus for PCR diagnosis, the apparatus including a transmitter including a multi-wavelength light source for outputting a plurality of light source signals, and configured to apply the plurality of light source signals to each of a plurality of DNA cells through an optical fiber bundle including a plurality of optical fibers connected to an optical splitter, wherein the plurality of DNA cells is included in a PCR chip and each of the plurality of DNA cells includes a plurality of DNAs, a code generator configured to generate a plurality of code signals corresponding to the plurality of light source signals, respectively, wherein the plurality of code signals is a Walsh code, and a receiver configured to receive light source reflection data including a plurality of light source reflection signals received through the optical fiber bundle from each of the DNA cells, to which the plurality of light source signals is applied, obtain light source power for each of the plurality of code signals for each of the DNA cells based on the light source reflection data, receive fluorescence data including a plurality of fluorescence signals received through the optical fiber bundle from a phosphor attached to each of the plurality of DNAs, to which the plurality of light source signals is applied, obtain fluorescence power for each of the plurality of code signals for each of the DNA cells based on the fluorescence data, and normalize the light source power and the fluorescence power for each of the DNA cells.

The light source power may be obtained for each of the plurality of code signals for each of the DNA cells by a dot product of the plurality of code signals and the light source reflection data including the plurality of light source reflection signals reflected from each of the DNA cells in response to the light source signal from each of the DNA cells, to which the plurality of light source signals is applied.

The fluorescence power may be obtained for each of the plurality of code signals for each of the DNA cells by a dot product of the plurality of code signals and the fluorescence data including the plurality of fluorescence signals emitted from a phosphor attached to each of the plurality of DNAs, to which the plurality of light source signals is applied.

The receiver may be configured to normalize the light source power and the fluorescence power for each of the plurality of code signals for each of the DNA cells by a ratio of the fluorescence power to the light source power.

The optical fiber bundle may include an optical fiber for applying the plurality of light source signals, an optical fiber for receiving the light source reflection data including the plurality of light source reflection signals, and an optical fiber for receiving the fluorescence data including the plurality of fluorescence signals.

A filter for attenuating an intensity of the light source reflection data may be coated on one end of the optical fiber for receiving the light source reflection data, and a filter for blocking the light source reflection data and passing only the fluorescence data may be coated on one end of the optical fiber for receiving the fluorescence data.

According to still another aspect, there is provided an operating method performed by an apparatus, the method including applying, using a transmitter including a multi-wavelength light source for outputting a plurality of light source signals, the plurality of light source signals to a side surface or a rear surface of a PCR chip including a plurality of DNA cells, wherein each of the plurality of DNA cells includes a plurality of DNAs and the plurality of light source signals corresponds to a plurality of code signals generated by a code generator, respectively, obtaining light source power for each of the plurality of code signals for each of the DNA cells based on light source reflection data including a plurality of light source reflection signals received by a receiver from each of the DNA cells, to which the plurality of light source signals is applied, obtaining fluorescence power for each of the plurality of code signals for each of the DNA cells based on fluorescence data including a plurality of fluorescence signals received by the receiver from a phosphor attached to each of the plurality of DNAs, to which the plurality of light source signals is applied, and normalizing the light source power and the fluorescence power for each of the DNA cells by the receiver.

The obtaining of the light source power for each of the plurality of code signals may include obtaining the light source power for each of the plurality of code signals for each of the DNA cells by a dot product of the plurality of code signals and the light source reflection data including the plurality of light source reflection signals reflected from each of the DNA cells in response to the light source signal from each of the DNA cells, to which the plurality of light source signals is applied.

The obtaining of the fluorescence power for each of the plurality of code signals may include obtaining the fluorescence power for each of the plurality of code signals for each of the DNA cells by a dot product of the plurality of code signals and the fluorescence data including the plurality of fluorescence signals emitted from a phosphor attached to each of the plurality of DNAs, to which the plurality of light source signals is applied.

The normalizing may include normalizing the light source power and the fluorescence power for each of the plurality of code signals for each of the DNA cells by a ratio of the fluorescence power to the light source power.

The receiver may include a camera configured to receive the light source reflection data and the fluorescence data, and the camera may be configured to receive the light source reflection data and the fluorescence data through two optical fibers connected to the receiver.

The receiver may include a first filter configured to, for one of the two optical fibers, block the light source reflection data and pass the fluorescence data, and a second filter configured to, for the other one of the two optical fibers, attenuate an intensity of the light source reflection data.

One of the two optical fibers may have an end connected to the receiver, where a first filter configured to block the light source reflection data and pass the fluorescence data is coated, and the other one of the two optical fibers may have an end connected to the receiver, where a second filter configured to attenuate an intensity of the light source reflection data is coated.

Additional aspects of example embodiments will be set forth in part in the description which follows and, in part, will be apparent from the description, or may be learned by practice of the disclosure.

According to an embodiment of the present disclosure, the apparatus for PCR diagnosis may receive the light source reflection data and the fluorescence data using the optical fiber and normalize the light source power and the fluorescence power using this, thereby improving accuracy.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
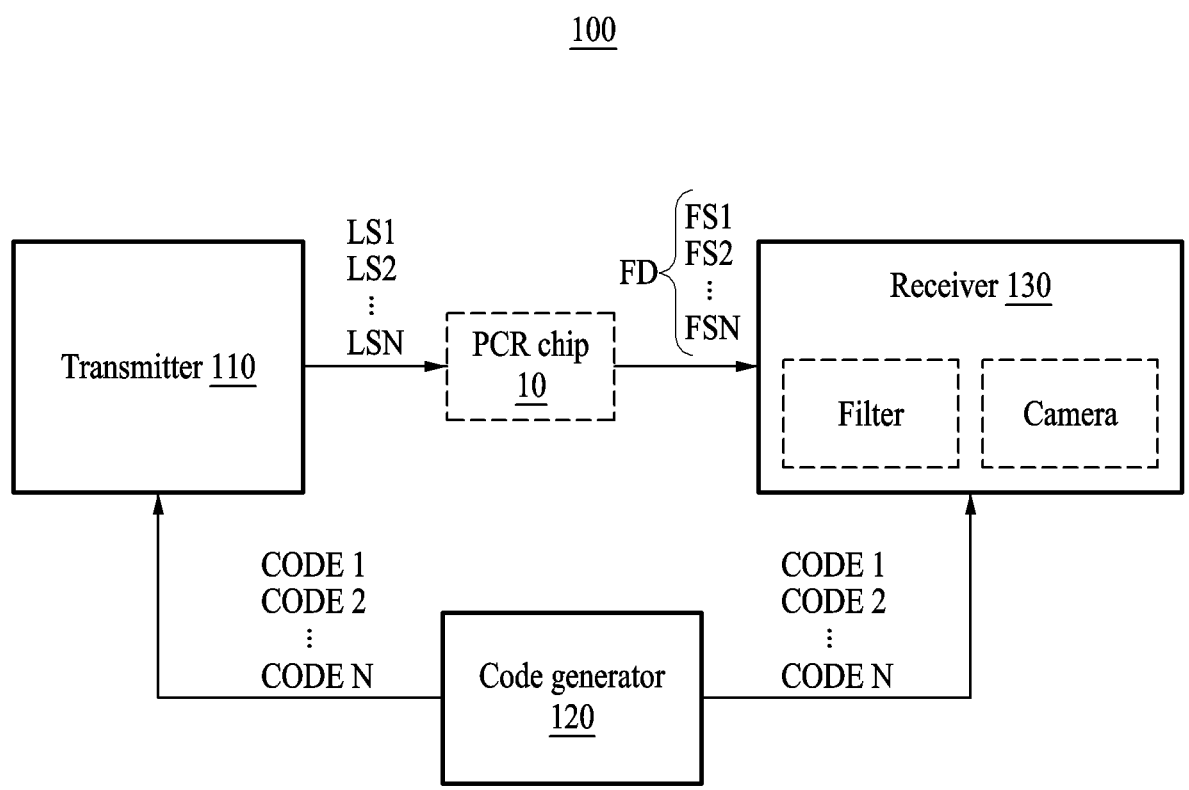
FIG. 1 illustrates an apparatus for polymerase chain reaction (PCR) diagnosis according to an embodiment.

Hereinafter, embodiments will be described in detail with reference to the accompanying drawings. The scope of the right, however, should not be construed as limited to the embodiments set forth herein. In the drawings, like reference numerals are used for like elements.

Various modifications may be made to the embodiments. Here, the embodiments are not construed as limited to the disclosure and should be understood to include all changes, equivalents, and replacements within the idea and the technical scope of the disclosure.

Although terms of "first" or "second" are used to explain various components, the components are not limited to the terms. These terms should be used only to distinguish one component from another component. For example, a first component may be referred to as a second component, and similarly the second component may also be referred to as the first component.

The terminology used herein is for the purpose of describing particular embodiments only and is not to be limiting of the embodiments. As used herein, the singular forms "a", "an", and "the" are intended to include the plural forms as well, unless the context clearly indicates otherwise. As used herein, "A or B", "at least one of A and B", "at least one of A or B", "A, B or C", "at least one of A, B and C", and "at least one of A, B, or C," each of which may include any one of the items listed together in the corresponding one of the phrases, or all possible combinations thereof. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the embodiments with reference to the accompanying drawings, like reference numerals refer to like constituent elements and a repeated description related thereto will be omitted. In the description of embodiments, detailed description of well-known related structures or functions will be omitted when it is deemed that such description will cause ambiguous interpretation of the present disclosure.

Hereinafter, embodiments will be described in detail with reference to the accompanying drawings.

FIG. 1 illustrates an apparatus 100 for polymerase chain reaction (PCR) diagnosis according to an embodiment.

The apparatus 100 for PCR diagnosis may apply a plurality of light source signals LS1 to LSN to a PCR chip 10 including a plurality of DNA cells each including a plurality of DNAs to which a phosphor is attached. The phosphor attached to each of DNAs in the plurality of DNA cells of the PCR chip 10 may emit fluorescence signals FS1 to FSN in response to the input light source signals LS1 to LSN. The apparatus 100 for PCR diagnosis may receive the fluorescence signals FS1 to FSN emitted from the plurality of DNA cells of the PCR chip 10, and detect a plurality of DNAs to be analyzed. The apparatus 100 for PCR diagnosis may include a transmitter 110, a code generator 120, and a receiver 130.

The transmitter 110 may include a plurality of multi-wavelength light sources for applying signals to the plurality of DNA cells of the PCR chip 10. For example, each of the plurality of light sources may be one of a laser diode (LD) or a light emitting diode (LED) having a limited wavelength range. Hereinafter, for a clear description, it is assumed that the plurality of light sources in the present disclosure are LD, but the present disclosure is not limited thereto. In addition, the light source of the present disclosure hereinafter means a multi-wavelength light source. The number of light sources may correspond to the number of different phosphors attached to the plurality of DNAs in the plurality of DNA cells of the PCR chip 10.

The plurality of light source signals LS1 to LSN may be signals to be output from the plurality of light sources, which are modulated based on one of a plurality of code signals CODE1 to CODEN received from the code generator 120. The transmitter 110 may include at least one of a circuit, software, or firmware for modulating signals to be output from the plurality of light sources based on one of the plurality of code signals CODE1 to CODEN.

For example, a level of a signal to be output from the plurality of light sources may be the same as an original level while a level of a code signal maintains a logic high value, and may be modulated to be 0 while the level of the code signal maintains a logic low value. For example, the signal to be output from the plurality of light sources may be modulated by a pulse amplitude modulation (PAM) method based on one of the plurality of code signals CODE1 to CODEN.

The transmitter 110 may include an optical fiber bundle including a plurality of optical fibers for applying the modulated light source signals LS1 to LSN to the plurality of DNA cells of the PCR chip 10. The light source signals LS1 to LSN having different wavelengths may be transmitted through corresponding optical fibers, and may be combined in one output optical fiber through an optical fiber combiner that uses wavelength division multiplexing (WDM) or space division multiplexing. The output optical fiber may include an optical splitter at an end thereof, and light source signals LS1 to LSN having different wavelengths may be applied to a plurality of DNAs through the optical splitter.

The code generator 120 may generate the plurality of code signals CODE1 to CODEN for modulating signals to be output from the plurality of light sources of the transmitter 110. For example, each of the plurality of code signals CODE1 to CODEN may be a pulse signal having a logic high value or a logic low value. In particular, the plurality of code signals CODE1 to CODEN generated by the code generator 120 of the present disclosure may be orthogonal to each other. That is, the plurality of code signals CODE1 to CODEN may be Walsh codes. The code generator 120 may modulate signals to be output from the light sources by applying one of the plurality of code signals CODE1 to CODEN orthogonal to each other to each of the light sources having different wavelengths.

Specifically, a level of the modulated light source signals LS1 to LSN is the same as an original level of a signal output from a light source while a level of a corresponding code signal maintains a logic high level, and may be 0, at which the light source is turned off, while the level of the corresponding code signal maintains a logic low value. In other words, the modulated light source signals LS1 to LSN may be applied to the plurality of DNA cells of the PCR chip 10 while the level of the corresponding code signal maintains a logic high value.

For example, the time at which the signal level starts to rise from a logic low value to a logic high value and the time at which the signal level starts to fall from a logic high value to a logic low value may be different for each of the code signals CODE1 to CODEN applied to the respective light sources having different wavelengths. Accordingly, the light source signals LS1 to LSN having different wavelengths may be temporally distributed and applied to the plurality of DNA cells of the PCR chip 10. In addition, the code generator 120 may transmit the generated code signals CODE1 to CODEN to the receiver 130. The code signals CODE1 to CODEN orthogonal to each other of the present disclosure will be described in more detail with reference to FIGS. 2A and 2B.

Different phosphors may be attached to each of the plurality of DNAs in the plurality of DNA cells inside the PCR chip 10. The different phosphors may absorb the light source signals LS1 to LSN having different wavelengths. A phosphor attached to each DNA may absorb a related light source signal and emit a fluorescence signal. For example, the phosphor may be a SYBR green phosphor that absorbs a light source having a wavelength of 530 nm or less and emits a fluorescence signal having a wavelength of 550 nm or more.

Therefore, the phosphor attached to each DNA of the present disclosure may absorb the light source signals LS1 to LSN having different wavelengths at different times determined based on the code signals CODE1 to CODEN, and may emit the fluorescence signals FS1 to FSN each corresponding to a wavelength of the absorbed light source signal LS. The fluorescence signals FS1 to FSN emitted from the phosphors may be provided to the receiver 130.

The receiver 130 may receive fluorescence data FD and light source reflection data. The fluorescence data may include the fluorescence signals FS1 to FSN emitted from the phosphors attached to each DNA in the plurality of DNA cells in the PCR chip 10. The light source reflection data may include a plurality of light source reflection signals obtained by reflection of the light source signals LS1 to LSN from the plurality of DNA cells in the PCR chip 10. The receiver 130 may be connected to an optical fiber bundle to receive the fluorescence data FD and the light source reflection data. The receiver 130 may include a filter for removing the light source reflection data for an optical fiber that receives the fluorescence data FD. The receiver 130 may include a neutral density (ND) filter that attenuates an intensity of the light source reflection data, for an optical fiber that receives light source reflection data having a high intensity. The ND filter may attenuate not only the intensity of the light source reflection data but also the intensity of the fluorescence data at the same ratio. In addition, the receiver 130 may include a camera for converting the fluorescence data FD and the light source reflection data into electrical signals.

Therefore, the receiver 130 may receive only the fluorescence data FD emitted from the plurality of DNA cells in the PCR chip 10 by removing, through the filter, the light source reflection data that is reflected from the plurality of DNA cells in the PCR chip 10 and transmitted through the optical fiber bundles. Also, the receiver 130 may reduce the intensity of the fluorescence data FD emitted from the plurality of DNA cells in the PCR chip 10 through the ND filter, and attenuate and receive the light source reflection data having a high intensity that is reflected from the plurality of DNA cells in the PCR chip 10 and transmitted through the optical fiber bundles. In addition, the fluorescence data FD and the light source reflection data may be converted into electrical signals by the camera.

Furthermore, the receiver 130 may receive the plurality of code signals CODE1 to CODEN orthogonal to each other from the code generator 120. In particular, the receiver 130 may perform the dot product on the fluorescence data FD and the light source reflection data using the plurality of code signals CODE1 to CODEN, and receive a result thereof as fluorescence power and light source power. The receiver 130 may include at least one of a circuit, software, or firmware for performing the dot product on the fluorescence data FD and the light source reflection data using the plurality of code signals CODE1 to CODEN. A specific embodiment in which the dot product is performed on the fluorescence data FD and the light source reflection data using the plurality code signals CODE1 to CODEN will be described in more detail with reference to FIGS. 2A and 2B below.

Among the fluorescence signals FS1 to FSN included in the input fluorescence data FD, fluorescence signals having coding coinciding with that of code signals are not orthogonal to the code signals, and therefore, the fluorescence signals may be accumulated when the dot product is performed on the fluorescence data FD and the code signal (that is, the fluorescence signal may have a signal intensity higher than that of an original fluorescence signal). On the other hand, fluorescence signals having coding not coinciding with that of code signals are orthogonal to the code signals, and therefore, the fluorescence signals may not be accumulated, even if the dot product is performed on the fluorescence data FD and the code signal. By doing so, the fluorescence signals coinciding with the received code signals may be summed through the dot product to obtain a high signal intensity, and thus, the gain may increase and the DNA replication cycle of a PCR system may be minimized.

Similarly, among the light source reflection signals included in the light source reflection data, light source reflection signals having coding coinciding with that of code signals are not orthogonal to the code signals, and therefore, the light source reflection signals may be accumulated when the dot product is performed on the light source reflection data and the code signals. On the other hand, the light source reflection signals having coding not coinciding with that of code signals are orthogonal to the code signals, and therefore, the light source reflection signals may not be accumulated even if the dot product is performed on the light source reflection data and the code signals.

Figures 2A, 2B:
FIG. 2A illustrates an example of a code signal generated by a code generator of FIG. 1 according to an embodiment.
FIG. 2B illustrates an example of performing the dot product on codes and fluorescence data received by a camera of a receiver according to an embodiment.

FIG. 2A illustrates an example of a code signal generated by a code generator of FIG. 1 according to an embodiment. As described above with reference to FIG. 1, the code signals CODE1 to CODEN of the present disclosure may be pulse signals having a logic high value (indicated by "1" in FIG. 2A) or a logic low value (indicated by "0" in FIG. 2A). In addition, the code signals CODE1 to CODEN of the present disclosure are orthogonal to each other. That is, the code signals CODE1 to CODEN of the present disclosure may be Walsh codes. Hereinafter, description will be made with reference to FIG. 1 together with FIG. 2A.

For a clear description, it is assumed that the transmitter 110 includes six light sources LD1 to LD6 having different wavelengths and the six light sources LD1 to LD6 output first to sixth light source signals LS1 to LS6, respectively. Also, it is assumed that the code generator 120 generates six code signals CODE1 to CODE6 which respectively correspond to the six light source signals LS1 to LS6 and are orthogonal to each other. In addition, it is assumed that a length of each of the code signals CODE1 to CODE6 is 16 bits. However, the present disclosure is not limited thereto, and the number of light sources, the number of code signals, or the length of code signals may vary.

The time during which the level of each of the code signals CODE1 to CODE6 is maintained as a logic high value (i.e., a duration of 1) and the time during which the level of each of the code signals is maintained as a logic low value (i.e., a duration of 0) may be changed according to the performance of the receiver 130. Also, as the total number of bits of the code signal increases, the gain may increase.

In each of the code signals CODE1 to CODE6 orthogonal to each other, the number of 1 (i.e., the total time during which the level is maintained as the logic high value) and the number of 0 (i.e., the total time during which the level is maintained as the logic low value) are equal to each other. In a case of code signals orthogonal to each other, a result of substituting a digit 1 of each of the code signals CODE1 to CODE6 with −1, substituting a digit 0 with 1, and performing the dot product between the code signals may be 0.

For example, the first code signal CODE1 and the second code signal CODE2, in which the digits 1 and 0 are substituted with −1 and 1, are as follows.

CODE1: −1, 1, 1, −1, 1, −1, −1, 1, 1, −1, −1, 1, −1, 1, 1, −1

CODE2: 1, −1, −1, 1, −1, 1, 1, −1, 1, −1, −1, 1, −1, 1, 1, −1

When the dot product is performed, it is calculated as (−1)*1+1*(−1)+1*(−1)+(−1)*1+1*(−1)+(−1)*1+(−1)*1+1*(−1)+1*1+(−1)*(−1)+(−1)*(−1)+1*1+(−1)*(−1)+1*1+1*1+(−1)*(−1), and a result thereof is 0. Conversely, even if the digit 1 is substituted with 1 and the digit 0 is substituted with −1, the result is the same which is 0. When the dot product is performed on any two code signals among remaining code signals by the same method as described above, a result thereof is 0. That is, it may be confirmed that the code signals CODE1 to CODE6 of FIG. 2A are orthogonal to each other.

As described above with reference to FIG. 1, the code signals CODE1 to CODE6 orthogonal to each other may be applied to the transmitter 110 and modulate the light source signals having different wavelengths. That is, the light source signals having different wavelengths may be coded to be orthogonal to each other, and fluorescence signals emitted by the plurality of DNAs in the plurality of DNA cells of the PCR chip 10 in response to the light source signals may be orthogonal to each other. Thus, the fluorescence signals and code signals may also be orthogonal to each other.

For example, a result of the dot product of a fluorescence signal generated based on a light source signal, to which the first code signal CODE1 is applied, and the second code signal CODE2 may be 0. However, since the phosphor actually attached to DNA receives not only the light source signals but also a noise or interference signal, a result of the dot product of the fluorescence signal and the code signal orthogonal to each other may be a value close to 0 rather than 0.

For example, a level of a fluorescence signal corresponding to a period in which the level of the code signal is a logic high value (i.e., a period in which a value of the code signal is 1) may be a value depending on the number of PCR cycles, and a level of a fluorescence signal corresponding to a period in which the level of the code signal is a logic low value (i.e., a period in which the value of the code signal is 0) may be a noise or an interference signal caused by another nearby light source. For example, the value depending on the number of PCR cycles may be greater than a magnitude of the noise or interference signal.

Specifically, it is assumed that the six code signals CODE1 to CODE6 modulate the six light source signals LS1 to LS6 having different wavelengths and the six light source signals LS1 to LS6 are applied to the plurality of DNA cells of the PCR chip 10 for the PCR at the same time. At this time, it is assumed that the PCR chip 10 includes n DNA cells in n channels, and each DNA cell contains different DNAs, to which six phosphors are attached. Fluorescence data including six fluorescence signals emitted from a first DNA cell may be provided to the receiver 130, and fluorescence data including six fluorescence signals emitted from a second DNA cell may be provided to the receiver 130. Similarly, fluorescence data including six fluorescence signals emitted from an n-th DNA cell may be provided to the receiver 130. Since it is previously assumed that the length of each of the code signals CODE1 to CODE6 is 16 bits, the length of the fluorescence data received by the receiver 130 is also 16 bits. For example, values of the fluorescence data DS1 received by the receiver may be expressed as a1, a2, . . . , a16.

FIG. 2B illustrates an example of performing the dot product on codes and fluorescence data received by a camera of a receiver according to an embodiment.

As described above with reference to FIG. 1, fluorescence data may include a plurality of fluorescence signals. For example, the fluorescence data DS1 may be a signal obtained by summing the six fluorescence signals FS1 to FS6 emitted from the first DNA cell.

For example, when the dot product is performed on the fluorescence data DS1 and the first code signal CODE1, a cumulative sum of the first fluorescence signal FS1 emitted by the first light source signal LS1, that is, fluorescence power according to the application of the first light source signal LS1 may be obtained. Similarly, when the dot product is performed on the fluorescence data DS1 and the sixth code signal CODE6, a cumulative sum of the sixth fluorescence signal FS6 emitted by the sixth light source signal LS6, that is, fluorescence power according to the application of the sixth light source signal LS6 may be obtained. Accordingly, the fluorescence power may be calculated for each of the plurality of code signals by the dot product of the plurality of code signals with the fluorescence data DS1.

For example, for the dot product of the fluorescence data DS1 and the first code signal CODE1, the first code signal CODE1 may be transformed by substituting the digit 0 with −1 and substituting the digit 1 with 1, and then the dot product may be performed on the transformed first code signal CODE1 and the fluorescence data DS1. As described above, a result of the dot product is fluorescence power that is a cumulative sum of the first fluorescence signal FS1 emitted when the first light source signal LS1 is applied to the first DNA cell. In other words, this cumulative sum may correspond to a signal obtained by summing the first fluorescence signal FS1 received by the receiver 130 based on the logic generated by the light source signal LS1 in the first light source LD1.

Referring to FIG. 2B, the result of the dot product calculated as described above (CODE1·S1; the cumulative sum of the first fluorescence signal FS1 received by the receiver 130) is $1*a1+(-1)*a2+(-1)*a3+1*a4+(-1)*a5+1*a6+1*a7+(-1)*a8+(-1)*a9+1*a10+1*a11+(-1)*a12+1*a13+(-1)*a14+(-1)*a15+1*a16$.

In this case, the cumulative sum of the first fluorescence signal FS1 may be a value accumulated by the number of 1s included in the corresponding first code signal CODE1 compared to the first fluorescence signal FS1. That is, in the above example, since the number of is included in the first code signal CODE1 is eight, the cumulative sum of the first fluorescence signal FS1 may have the gain eight times greater than the first fluorescence signal FS1. Since the first fluorescence signal FS1 generated by the first light source signal LS1 is orthogonal to the fluorescence signals (e.g., FS2 to FS6) generated with other wavelengths, it does not affect the cumulative sum of other fluorescence signals.

Similarly, the cumulative sum of each of the second to sixth fluorescence signals FS2 to FS6 generated by applying the second to sixth light source signals LS2 to LS6 to the first DNA cell may be calculated by the dot product of the second to sixth code signals CODE2 to CODE6 to the fluorescence data DS1 received by each camera. A cumulative sum of fluorescence signals formed by other DNAs in other DNA cells of the PCR chip 10 may be calculated by the same method.

As described above, the fluorescence signal emitted from each DNA included in each of the DNA cells of the PCR chip 10 may be separated by the dot product of a corresponding code signal and fluorescence data received by the receiver. In addition, since the plurality of light source signals are applied to each of the DNA cells at the same time, the processes described above may be processed in parallel and the PCR may be rapidly performed. Furthermore, for convenience of description, the method of calculating the cumulative sum of the fluorescence signal, that is, the fluorescence power by the dot product of the fluorescence data and the code signal is described, however, a cumulative sum of a light source reflection signal, that is, light source power may be calculated by the dot product of the light source reflection data and the code signal by the same method.

However, the present disclosure is not limited to those described above with reference to FIGS. 2A and 2B, and the code signals generated by the code generator 120 may show a logic high value ("1") and a logic low value ("0") alternately, unlike the first to sixth code signals CODE1 to CODE6 shown in FIGS. 2A and 2B, and may be pulse signals orthogonal to each other. Also, the dot product of the fluorescence data and the code signal may be performed by a method different from that described above.

FIG. 3 is a diagram illustrating an operation of an electronic apparatus for directly applying a light source signal to a PCR chip according to an embodiment.

Figure 3A:
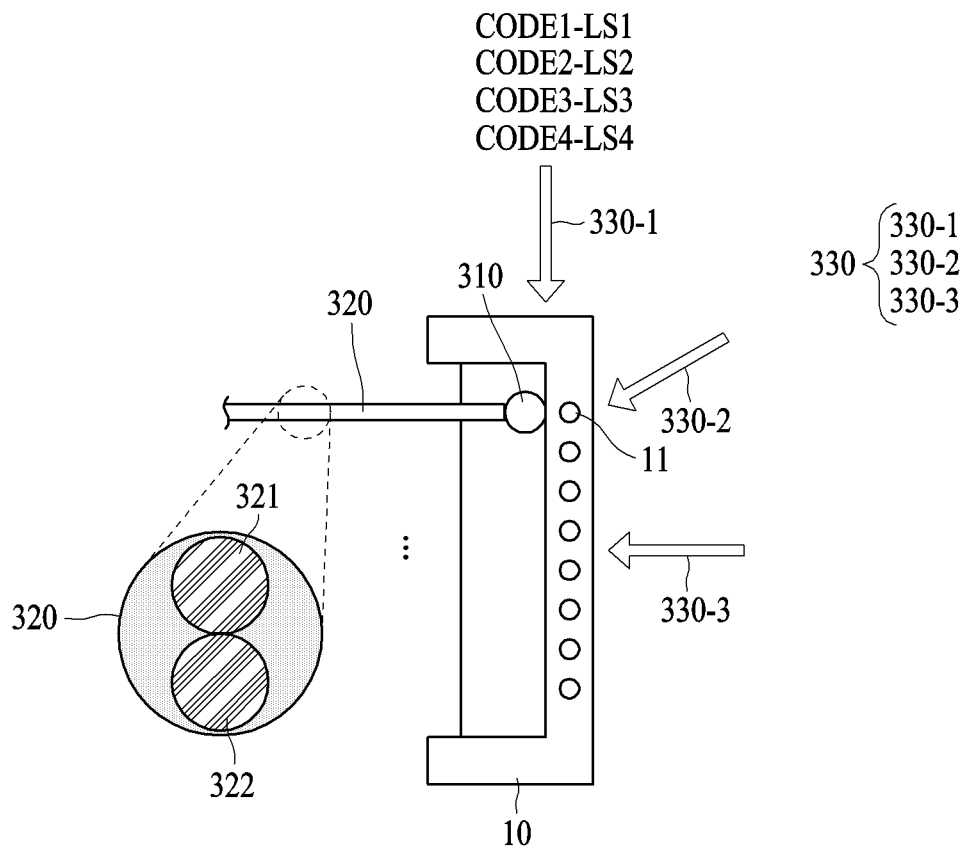
FIG. 3A and FIG. 3B is a diagram illustrating an operation of an apparatus for directly applying a light source signal to a PCR chip according to an embodiment.
Figure 3B:
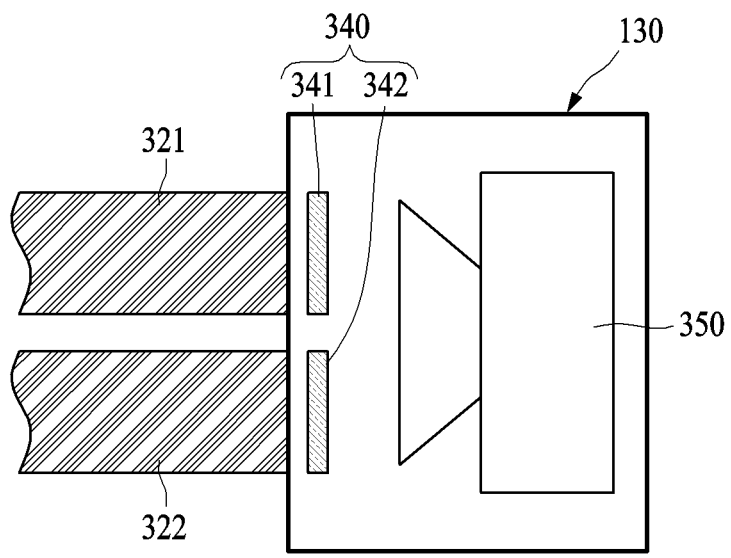

FIG. 3A shows the PCR chip 10 to which a light source signal is directly applied by a transmitter without passing through an optical fiber. FIG. 3B shows the receiver 130 configured to receive a light source reflection signal and fluorescence data.

Hereinafter, for convenience of description, the description will be made based on the DNA cell 11 included in the PCR chip 10. However, embodiments are not limited thereto and may be applied to all DNA cells included in the PCR chip 10.

Referring to FIG. 3A, the transmitter may directly apply a plurality of light source signals modulated by a plurality of code signals to the PCR chip 10 in various directions 330 without passing through an optical fiber. For example, the transmitter may apply light source signals in a lateral direction 330-1, an oblique direction 330-2, or a rear direction 330-3 of the PCR chip 10. Various directions 330 for applying the light source signal shown in the drawing are merely examples, and the present disclosure is not limited thereto.

The transmitter may directly apply the first light source signal LS1 modulated by the first code signal CODE1, the second light source signal LS2 modulated by the second code signal CODE2, the third light source signal LS3 modulated by the third code signal CODE3, and the fourth light source signal LS4 modulated by the fourth code signal CODE4 to the PCR chip 10. For convenience of description, it is assumed that the number of code signals is four, but the present disclosure is not limited thereto.

A plurality of light source signals applied to the DNA cell 11 included in the PCR chip may be reflected. A plurality of signals emitted, in response to the light source signals, from the DNA cell 11, to which the plurality of light source signals is applied, may be a plurality of light source reflection signals. Light source reflection data may include the plurality of light source reflection signals.

The light source reflection data may be transmitted to the receiver 130 through a first optical fiber 321 included in an optical fiber bundle 320. The light source reflection data may be focused on the optical fiber bundle 320 through a ball lens 310.

A phosphor attached to each of a plurality of DNAs included in the DNA cell 11 of the PCR chip 10, to which the plurality of light source signals is applied, may emit a plurality of fluorescence signals. Fluorescence data including the plurality of fluorescence signals may be transmitted to the receiver 130 through a second optical fiber 322 included in the optical fiber bundle 320. The fluorescence data including the plurality of fluorescence signals may be focused on the optical fiber bundle 320 through the ball lens 310.

Referring to FIG. 3B, the receiver 130 may be connected to the first optical fiber 321 and the second optical fiber 322. The receiver 130 may include a filter 340 that passes only necessary signals from signals received from the first optical fiber 321 and the second optical fiber 322. The receiver 130 may include a camera 350 that receives the signal which has passed through the filter 340 and converts the signal into an electrical signal.

The receiver 130 may include a second filter 341 capable of attenuating the intensity of fluorescence data and the intensity of light source reflection data received from the first optical fiber 321. The intensity of the light source reflection data may be greater than the intensity of the fluorescence data. Accordingly, the receiver 130 may reduce the intensity of the light source reflection data by using the second filter 341 in order to normalize the light source power using the light source reflection data and the fluorescence power using the fluorescence data. For example, the second filter 341 may be an ND filter.

The receiver 130 may include a first filter 342 that blocks light source reflection data corresponding to a noise among signals received from the second optical fiber 322, and passes only fluorescence data. For example, the first filter 342 may be a bandpass filter that blocks the light source reflection data and passes only the fluorescence data.

According to an embodiment, the second filter 341 may be coated on one end of the first optical fiber 321. The first filter 342 may be coated on one end of the second optical fiber 322. For example, the second filter 341 may be coated on a portion where the first optical fiber 321 is connected to the receiver 130 or a portion where the first optical fiber 321 receives light source reflection data from the DNA cell 11. For example, the first filter 342 may be coated on a portion where the second optical fiber 322 is connected to the receiver 130 or a portion where the second optical fiber 322 receives fluorescence data from the DNA cell 11.

The camera 350 may receive the light source reflection data and the fluorescence data that have passed through the filter 340, and convert them into electrical signals.

The receiver 130 may calculate light source power for each of the plurality of code signals by the dot product of the received light source reflection data and the plurality of code signals. The receiver 130 may calculate the light source power for each of the plurality of code signals with respect to each of the plurality of DNA cells included in the PCR chip 10. The receiver 130 may calculate fluorescence power for each of the plurality of code signals by the dot product of the received fluorescence data and the plurality of code signals. The receiver 130 may calculate the fluorescence power for each of the plurality of code signals with respect to each of the plurality of DNA cells included in the PCR chip 10. The method of performing the dot product described above with respect to FIG. 2 may be used for the method of performing the dot product of the plurality of code signals, and the light source reflection data and the fluorescence data.

The receiver 130 may normalize the light source power and the fluorescence power for each of the plurality of DNA cells using the light source power and the fluorescence power calculated for each of the plurality of code signals. The receiver 130 may normalize the light source power and the fluorescence power by a ratio of the fluorescence power to the light source power for each of the plurality of code signals for each of the plurality of DNA cells.

For example, it is assumed that the PCR chip 10 includes 10 channels of DNA cells. The receiver 130 may normalize the light source power and the fluorescence power by a ratio of the fluorescence power to the light source power for each of the plurality of code signals with respect to each of first to tenth DNA cells. For example, when the plurality of light source signals are applied to the PCR chip 10, the receiver 130 may calculate a ratio of the fluorescence power to the light source power according to the application of the plurality of light source signals with respect to each of the first to tenth DNA cells.

When a particular light source signal is applied, the receiver 130 may determine whether a bio-sample application process is saturated by using the ratio of the fluorescence power to the light source power for each of the plurality of DNA cells. When a difference between ratios of the fluorescence power to the light source power for the plurality of DNA cells is greater than or equal to a threshold value, the receiver 130 may determine that the bio-sample application process is saturated. For example, it is assumed that a light source signal is applied to the PCR chip 10 in the lateral direction 330-1, and the PCR chip includes 10 channels of DNA cells. At this time, when a ratio of the fluorescence power to the light source power of the first DNA cell which is closest to a portion, to which the light source signal is applied, is 0.8, and a ratio of the fluorescence power to the light source power of the tenth DNA cell which is farthest from the portion, to which the light source signal is applied, is 0.4, the fluorescence power of the tenth DNA cell is insufficient, that is, the amount of DNA expressed is small, and thus, the receiver 130 may determine that the bio-sample amplification is not yet saturated. On the other hand, when the ratio of the fluorescence power to the light source power of the first DNA cell is 0.8 and the ratio of the fluorescence power to the light source power of the tenth DNA cell which is farthest from the portion, to which the light source signal is applied, is 0.75, the receiver 130 may determine that the bio-sample amplification is saturated. A ratio value of the fluorescence power to the light source power described above is a random value set for the convenience of description, and this may vary according to a value of an attenuation filter (ND filter) for the intensity of reflected light.

Accordingly, the apparatus for PCR diagnosis may recognize the intensity of the light source signal applied to each DNA cell and the intensity of the fluorescence signal according to the application of the corresponding light source signal. Through this, a change of the intensity of the fluorescence signal according to the intensity of the applied light source signal may be recognized, and this may improve accuracy of the apparatus for PCR diagnosis.

Figure 4:
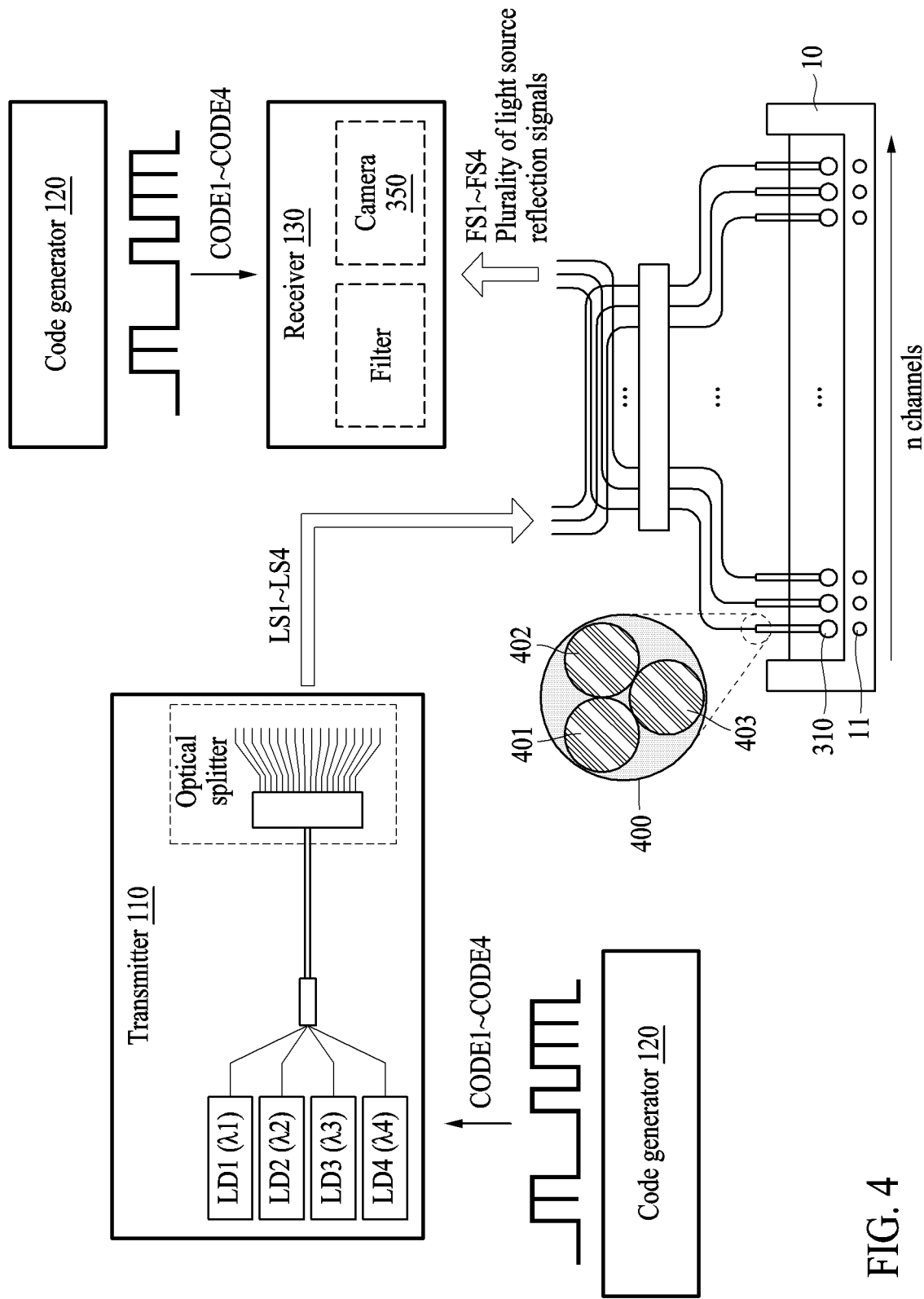
FIG. 4 is a diagram illustrating an operation of an apparatus for PCR diagnosis for applying a light source signal through an optical fiber according to an embodiment.

FIG. 4 is a diagram illustrating an operation of an apparatus for PCR diagnosis for applying a light source signal through an optical fiber according to an embodiment.

The PCR chip 10 shown in FIG. 4 may include a plurality of DNA cells including a plurality of DNAs. For example, the PCR chip 10 may include n-channels of DNA cells. A phosphor attached to the plurality of DNAs included in each of the DNA cells may absorb a light source signal having a corresponding wavelength and emit a fluorescence signal.

It is assumed that the number of different phosphors attached to the DNAs of each DNA cell is four in FIG. 4, and the transmitter 110 includes the first to fourth light sources LD1 to LD4 respectively corresponding to the four different phosphors. The first to fourth light sources may have different first to fourth wavelengths $\lambda 1$ to $\lambda 4$, respectively. However, the present disclosure is not limited thereto, and the number of DNA cells included in the PCR chip 10, the number of phosphors, and the number of light sources may be set differently from those shown in FIG. 4.

As described above with reference to FIG. 1, the first to fourth light source signals LS1 to LS4 may be combined in one output optical fiber through an optical fiber combiner that uses wavelength division multiplexing (WDM) or space division multiplexing. The output optical fiber may include an optical splitter at an end thereof, and the first to fourth light source signals LS1 to LS4 having different wavelengths $\lambda 1$ to $\lambda 4$ may be applied to the plurality of DNA cells through the optical splitter at the same time.

Specifically, an optical fiber bundle 400 may apply the light source signal to each of the plurality of DNA cells and receive light source reflection data and fluorescence data. The plurality of light source signals may be applied to the plurality of DNA cells at the same time through an optical fiber 401 applying the light source signal, which is one of optical fibers included in the optical fiber bundle 400.

Each of the light source signals applied to the plurality of DNA cells may be reflected by the plurality of DNA cells. Accordingly, first to fourth light source reflection signals may be emitted from the plurality of DNA cells. A plurality of pieces of light source reflection data including the first to fourth light source reflection signals may be transmitted to the receiver 130 through an optical fiber 402 receiving the light source reflection data, which is one of optical fibers included in the optical fiber bundle 400. The received light source reflection data may be converted into electrical signals by the camera 350.

A phosphor attached to the plurality of DNAs included in the plurality of DNA cells may absorb the first to fourth light source signals through a plurality of optical fiber bundles at different times according to codes. Thus, the first to fourth fluorescence signals FS1 to FS4 may be emitted from the plurality of DNAs. The fluorescent data including the first to fourth fluorescent signals FS1 to FS4 emitted from each of the DNA cells of the PCR chip 10 may be transmitted to the receiver 130 through an optical fiber 403 that is included in the optical fiber bundle 400 and receives the fluorescent data. The received fluorescence data may be converted into an electrical signal by the camera 350.

The receiver 130 may perform the dot product on the transmitted light source reflection data and fluorescence data using the first to fourth code signals CODE1 to CODE4 received from the code generator 120. The receiver 130 may calculate the light source power and the fluorescence power through the dot product. The receiver 130 may normalize a ratio of the fluorescence power to the light source power for each of a plurality of code signals for each of a plurality of DNA cells using the calculated light source power and fluorescence power.

Meanwhile, the receiver 130 may include a filter to block signals that are erroneously received through an optical fiber. For example, the receiver 130 may include a filter for attenuating light source reflection data having a high intensity received through the optical fiber 402 that receives the light source reflection data, and a filter for blocking the light source reflection data received through the optical fiber 403 that receives the fluorescence data.

Figure 5A:
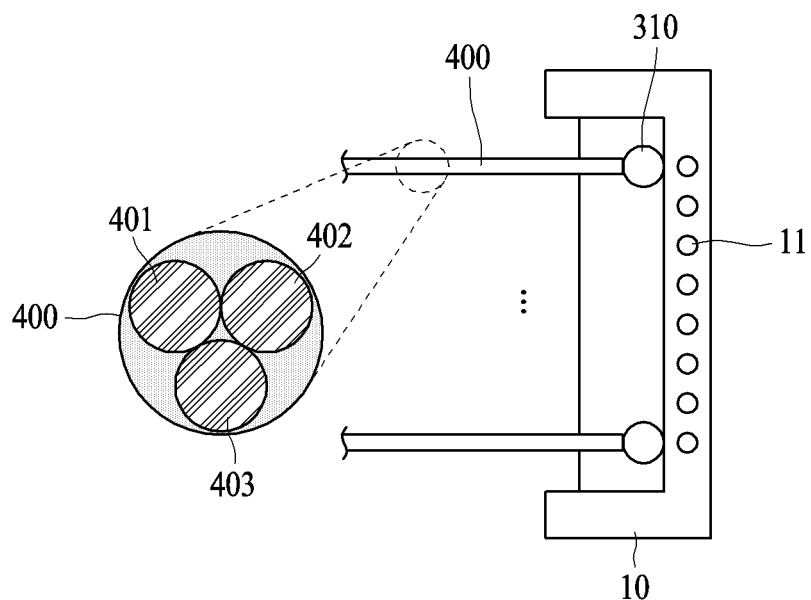
FIG. 5A and FIG. 5B is a diagram illustrating an example of applying a light source signal through an optical fiber according to an embodiment.
Figure 5B:
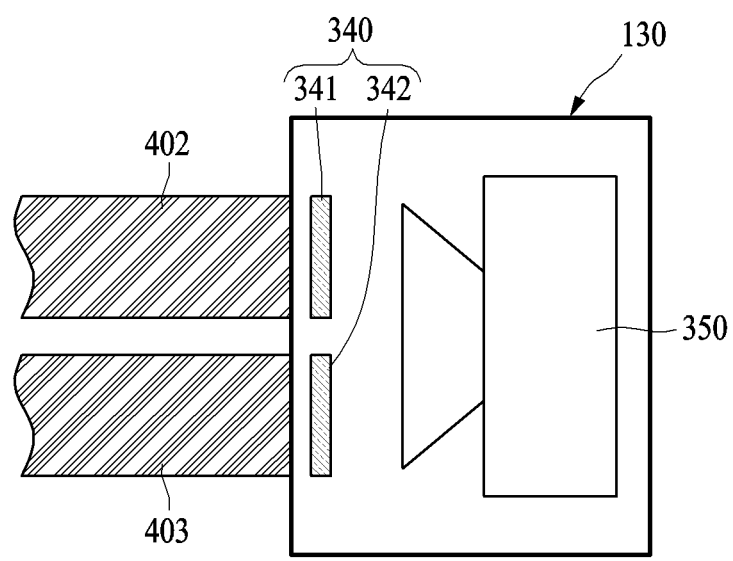

FIG. 5A and FIG. 5B is a diagram illustrating an example of applying a light source signal through an optical fiber according to an embodiment.

Hereinafter, for convenience of description, the description will be made based on the DNA cell 11 included in the PCR chip 10. However, embodiments are not limited thereto and may be applied to all DNA cells included in the PCR chip 10.

FIG. 5A shows the PCR chip 10 to which a light source signal is applied through an optical fiber. A transmitter may apply a plurality of light source signals modulated by a plurality of code signals to each of a plurality of DNA cells through the optical fiber 401 that is included in the optical fiber bundle 400 and applies a light source signal. For example, the transmitter may apply the plurality of light source signals to the DNA cell 11 through the optical fiber 401 that is included in the optical fiber bundle 400 and applies a light source signal.

The plurality of light source signals applied to the DNA cell 11 may be reflected. A plurality of signals emitted, in response to the light source signals, from the DNA cell 11, to which the plurality of light source signals is applied, may be a plurality of light source reflection signals. Light source reflection data may include the plurality of light source reflection signals.

The light source reflection data may be transmitted to the receiver 130 through the optical fiber 402 that is included in the optical fiber bundle 400 and receives the light source reflection data. The light source reflection data may be focused on the optical fiber bundle 400 through the ball lens 310.

A phosphor attached to each of a plurality of DNAs included in the DNA cell 11, to which the plurality of light source signals is applied, may emit a plurality of fluorescence signals. Fluorescence data including the plurality of fluorescence signals may be transmitted to the receiver 130 through the optical fiber 403 that is included in the optical fiber bundle 400 and receives the fluorescence data. The fluorescence data may be focused on the optical fiber bundle 400 through the ball lens 310.

FIG. 5B shows the receiver 130 that receives the fluorescence data and the light source reflection data.

The receiver 130 may include the filter 340 for blocking a signal corresponding to a noise among signals received through the optical fiber. The receiver 130 may include the second filter 341 for attenuating fluorescence data corresponding to a noise among signals received from the optical fiber 402 that receives light source reflection data, and attenuating the intensity of the light source reflection data. The second filter 341 may be an ND filter. Since the light source reflection data has the intensity higher than that of the fluorescence data, the intensity of the fluorescence data may be much smaller than that of the light source reflection data, when they pass through the second filter 341.

The receiver 130 may include the first filter 342 for blocking light source reflection data corresponding to a noise among signals received from the optical fiber 403 that receives fluorescence data, and passing only fluorescence data. The first filter may be a bandpass filter that blocks the light source reflection data and passes only the fluorescence data.

According to an embodiment, the second filter 341 may be coated on one end of the optical fiber 402 that receives the light source reflection data. The first filter 342 may be coated on one end of the optical fiber 403 that receives the fluorescence data. For example, the second filter 341 may be coated on a portion where the optical fiber 402 that receives the light source reflection data is connected to the receiver 130 or a portion where the optical fiber 402 that receives the light source reflection data receives light source reflection data from the DNA cell 11. For example, the first filter 342 may be coated on a portion where the optical fiber 403 that receives fluorescence data is connected to the receiver 130 or a portion where the optical fiber 403 that receives fluorescence data receives fluorescence data from the DNA cell 11.

The camera 350 may receive the light source reflection data and the fluorescence data that have passed through the filter 340, and convert them into electrical signals.

The receiver 130 may calculate light source power for each of the plurality of code signals by the dot product of the received light source reflection data and the plurality of code signals. The receiver 130 may calculate the light source power for each of the plurality of code signals with respect to each of the plurality of DNA cells included in the PCR chip 10. The receiver 130 may calculate fluorescence power for each of the plurality of code signals by the dot product of the received fluorescence data and the plurality of code signals. The receiver 130 may calculate the fluorescence power for each of the plurality of code signals with respect to each of the plurality of DNA cells included in the PCR chip 10. The method of performing the dot product described above with respect to FIG. 2 may be used for the method of performing the dot product of the plurality of code signals, and the light source reflection data and the fluorescence data.

The receiver 130 may normalize each of the plurality of DNA cells using the light source power and the fluorescence power calculated for each of the plurality of code signals. The receiver 130 may normalize the light source power and the fluorescence power by a ratio of the fluorescence power to the light source power for each of the plurality of code signals for each of the plurality of DNA cells.

For example, it is assumed that the PCR chip 10 includes 10 channels of DNA cells. The receiver 130 may normalize the light source power and the fluorescence power by a ratio of the fluorescence power to the light source power for each of the plurality of code signals for each of the first to tenth DNA cells. For example, when the plurality of light source signals are applied to the PCR chip 10, the receiver 130 may calculate a ratio of the fluorescence power to the light source power according to the application of the plurality of light source signals with respect to each of the first to tenth DNA cells.

When a particular light source signal is applied, the receiver 130 may determine whether a bio-sample application process is saturated by using the ratio of the fluorescence power to the light source power for each of the plurality of DNA cells. When a difference between ratios of the fluorescence power to the light source power for the plurality of DNA cells is greater than or equal to a threshold value, the receiver 130 may determine that the bio-sample application process is saturated. For example, it is assumed that light source signals are applied to the PCR chip 10 non-uniformly and the PCR chip includes 10 channels of DNA cells. At this time, in a case where a ratio of the fluorescence power to the light source power of a second DNA cell is 0.8 when a portion, to which a light source signal is strongly applied, is a second DNA, and a ratio of the fluorescence power to the light source power of a fifth DNA cell is 0.4 when a portion, to which a light source signal is weakly applied, is a fifth DNA, the fluorescence power of the fifth DNA cell is insufficient, that is, the amount of DNA expressed is small, and thus, the receiver 130 may determine that the bio-sample amplification is not yet saturated. On the other hand, when the ratio of the fluorescence power to the light source power of the second DNA cell is 0.8 and the ratio of the fluorescence power to the light source power of the fifth DNA cell is 0.75, the receiver 130 may determine that the bio-sample amplification is saturated. A ratio value of the fluorescence power to the light source power is a randomly set value, and the ratio value of the fluorescence power to the light source power may vary according to a value of an attenuation filter for the intensity of reflected light.

Figure 6A:
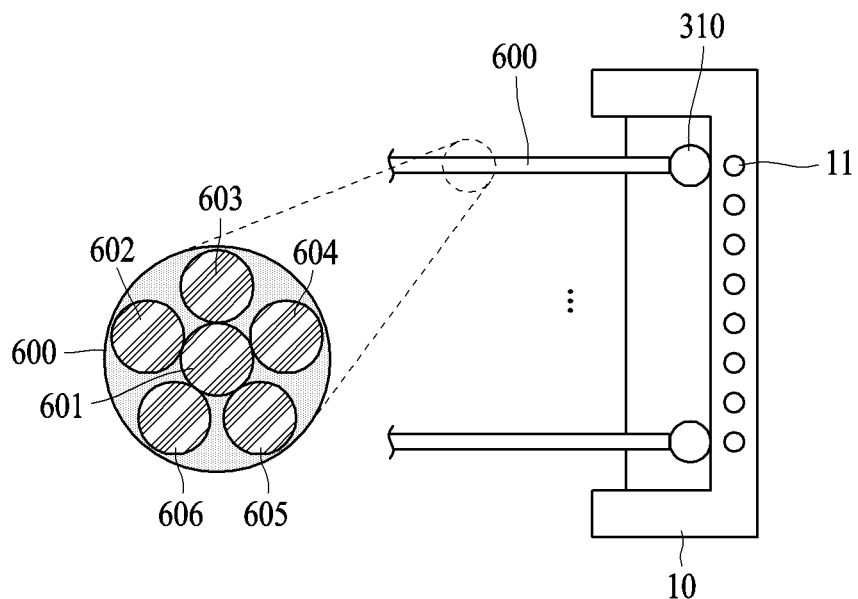
FIG. 6A and FIG. 6B is a diagram illustrating an example of applying a light source signal through an optical fiber according to an embodiment.
Figure 6B:
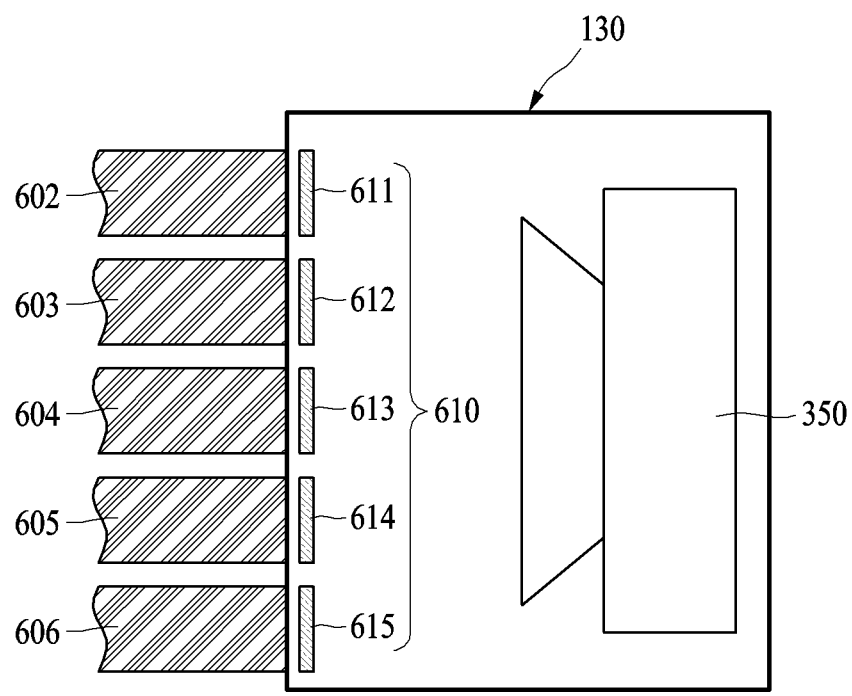

FIG. 6A and FIG. 6B is a diagram illustrating an example of applying a light source signal through an optical fiber according to an embodiment.

FIG. 6A shows the PCR chip 10 to which a light source signal is applied through an optical fiber. An optical fiber bundle 600 may include an optical fiber 601 for applying a light source signal, an optical fiber 602 for receiving light source reflection data, an optical fiber 603 for receiving a first fluorescence signal, an optical fiber 604 for receiving a second fluorescence signal, an optical fiber 605 for receiving a third fluorescence signal, and an optical fiber 606 for receiving a fourth fluorescence signal. However, the present disclosure is not limited thereto, and the number of optical fibers 603 to 606 for receiving the fluorescence signals may correspond to the number of code signals generated by a code generator.

A transmitter may apply a plurality of light source signals modulated by a plurality of code signals to each of a plurality of DNA cells through the optical fiber 601 that is included in the optical fiber bundle 600 and applies a light source signal. The optical fiber 601 for applying a light source signal may be positioned at the center of the optical fiber bundle.

A plurality of light source signals applied to the DNA cell 11 may be reflected. A plurality of signals emitted, in response to the light source signals, from the DNA cell 11, to which the plurality of light source signals is applied, may be a plurality of light source reflection signals. Light source reflection data may include the plurality of light source reflection signals.

The light source reflection data may be transmitted to the receiver 130 through the optical fiber 602 that is included in the optical fiber bundle 600 and receives the light source reflection data. The light source reflection data may be focused on the optical fiber bundle 600 through the ball lens 310.

A phosphor attached to each of a plurality of DNAs included in the DNA cell 11, to which the plurality of light source signals is applied, may emit a plurality of fluorescence signals. The plurality of fluorescence signals may be transmitted to the receiver 130 through the plurality of optical fibers 603 to 606 included in the optical fiber bundle. In a case of FIG. 6A and FIG. 6B, each of the plurality of fluorescence signals may be transmitted to the receiver 130 through each of the corresponding optical fibers 603 to 606, unlike the case of FIG. 5 in which the fluorescence data including the plurality of fluorescence signals is transmitted to the receiver 130 through the optical fiber 403 for receiving the fluorescence data, which is one of the optical fibers.

FIG. 6B shows the receiver 130 that receives a plurality of fluorescence signals and light source reflection data.

The receiver 130 may include a filter 610 for blocking a signal corresponding to a noise among signals received through the optical fiber.

The receiver 130 may include a filter 611 for attenuating light source reflection data having a high intensity and a fluorescence signal having a low intensity through the optical fiber 602. For example, the filter 611 may be an ND filter. The intensity of the light source reflection data may be relatively higher than the intensity of the fluorescence signal. Accordingly, the intensity of the fluorescence signal after passing through the filter 611 may be very small compared to the intensity of the light source reflection data.

The receiver 130 may include a filter 612 for passing only the first fluorescence signal through the optical fiber 603 and blocking other signals. The receiver 130 may include a filter 613 for passing only the second fluorescence signal through the optical fiber 604 and blocking other signals. The receiver 130 may include a filter 614 for passing only the third fluorescence signal through the optical fiber 605 and blocking other signals. The receiver 130 may include a filter 615 for passing only the fourth fluorescence signal through the optical fiber 606 and blocking other signals. For example, the plurality of filters 612 to 615 for passing only the fluorescence signals received by the optical fibers may be bandpass filters for passing only corresponding fluorescence signals.

According to an embodiment, the filter 611 may be coated on one end of the optical fiber 602 for receiving light source reflection data. The plurality of filters 612 to 615 for passing only the fluorescence signals received by the optical fibers may be coated on one ends of the plurality of optical fibers 603 to 606 for receiving the fluorescence signals. For example, the filter 611 may be coated on a portion where the optical fiber 602 receives light source reflection data from the DNA cell 11 or a portion where the optical fiber 602 is connected to the receiver 130. For example, the filter 612 may be coated on a portion where the optical fiber 603 receives light source reflection data from the DNA cell 11 or a portion where the optical fiber 603 is connected to the receiver 130.

The camera 350 may receive the light source reflection data and the plurality of fluorescence signals that have passed through the filter 340 and convert them into electrical signals.

The receiver 130 may calculate light source power for each of the plurality of code signals by the dot product of the received light source reflection data and the plurality of code signals. The receiver 130 may calculate the light source power for each of the plurality of code signals with respect to each of the plurality of DNA cells included in the PCR chip 10.

The receiver 130 may calculate fluorescence power for each code signal by the dot product of a corresponding fluorescence signal and a corresponding code signal for each of the received fluorescence signals. The receiver 130 may calculate light source reflection power and fluorescence power for each of a plurality of code signals for each of a plurality of DNA cells included in the PCR chip 10. For example, the receiver 130 may calculate the fluorescence power of the first code signal by the dot product of the first code signal corresponding to the first fluorescence signal with respect to the first fluorescence signal received through the optical fiber 603. The receiver 130 may calculate the fluorescence power of the first code signal for each of the plurality of DNA cells included in the PCR chip 10.

The receiver 130 may normalize the intensity of a fluorescence signal emitted by the phosphor attached to the DNA according to the intensity of the light source signal for each of the plurality of DNA cells using the light source power and the fluorescence power calculated for each of the plurality of code signals. The receiver 130 may normalize the intensity of the light source signal and the intensity of the fluorescence signal emitted by the phosphor attached to the DNA by a ratio of the fluorescence power to the light source power for each of the plurality of DNA cells.

The receiver 130 may determine whether the bio-sample amplification process is saturated using a result of the normalization. The receiver 130 may determine whether the bio-sample amplification process is saturated using the ratio of the fluorescence power to the light source power for each of the plurality of DNA cells. When a difference between ratios of the fluorescence power to the light source power for the plurality of DNA cells is greater than or equal to a threshold value, the receiver 130 may determine that the bio-sample application process is saturated. For example, it is assumed that the PCR chip includes 10 channels of DNA cells. At this time, when a ratio of the fluorescence power to the light source power of the first DNA cell is 0.8 and a ratio of the fluorescence power to the light source power of the tenth DNA cell is 0.4, the fluorescence power of the tenth DNA cell is insufficient, that is, the amount of DNA expressed is small, and thus, the receiver 130 may determine that the bio-sample amplification is not yet saturated. On the other hand, when the ratio of the fluorescence power to the light source power of the first DNA cell is 0.8 and the ratio of the fluorescence power to the light source power of the tenth DNA cell is 0.75, the receiver 130 may determine that the bio-sample amplification is saturated.

Figure 7:
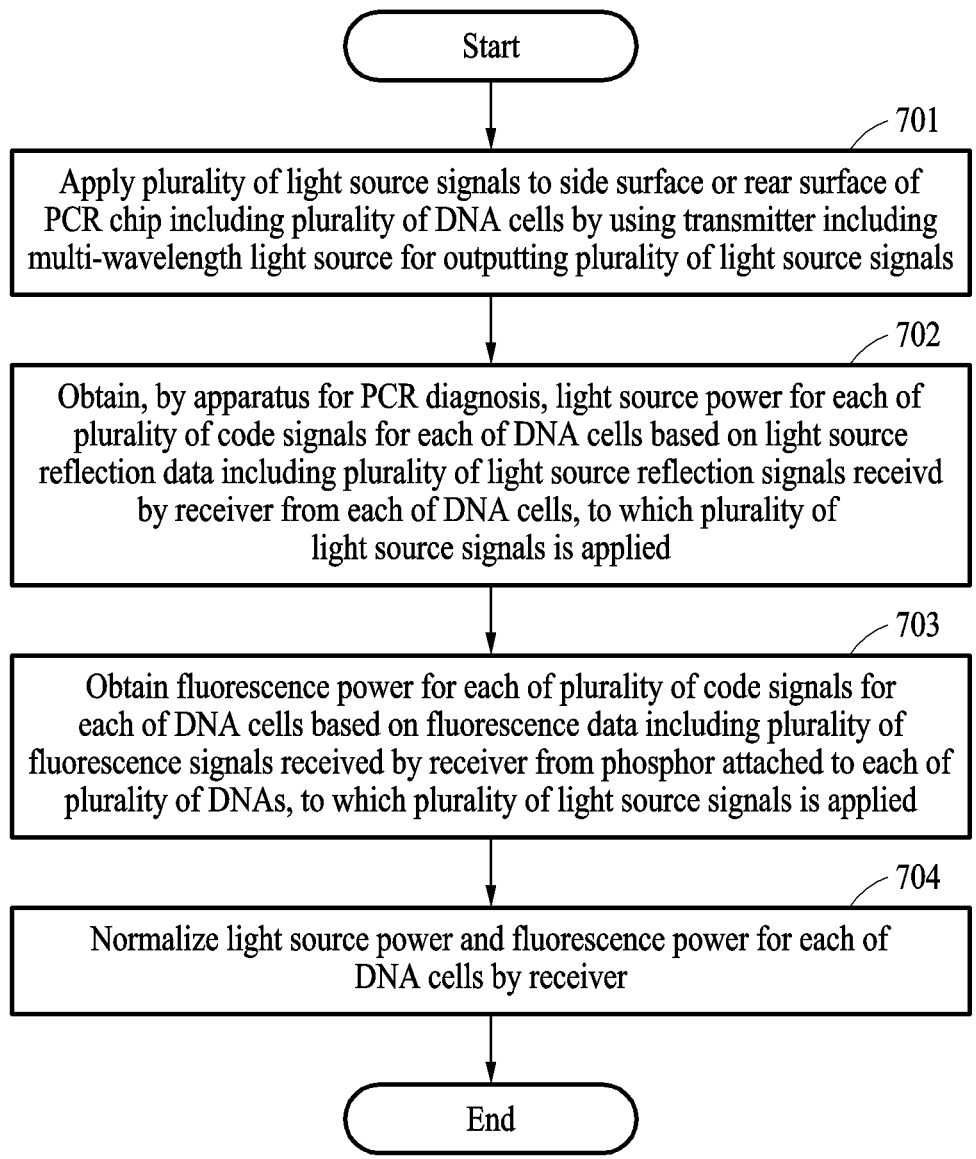
FIG. 7 is a diagram illustrating a method of operating an apparatus for PCR diagnosis according to an embodiment.

FIG. 7 is a diagram illustrating a method of operating an apparatus for PCR diagnosis according to an embodiment.

In the following embodiments, operations may be performed sequentially, but not necessarily performed sequentially. For example, the order of the operations may be changed and at least two of the operations may be performed in parallel. Operations 701 to 704 may be performed by an electronic apparatus for PCR diagnosis.

In operation 701, the apparatus for PCR diagnosis may apply a plurality of light source signals to a side surface or a rear surface of a PCR chip including a plurality of DNA cells by using a transmitter including a multi-wavelength light source for outputting a plurality of light source signals.

Each of the plurality of DNA cells may include a plurality of DNAs. The plurality of light source signals may correspond to a plurality of code signals generated by a code generator, respectively.

In operation 702, the apparatus for PCR diagnosis may obtain light source power for each of the plurality of code signals for each of the DNA cells based on light source reflection data including a plurality of light source reflection signals received by a receiver from each of the DNA cells, to which the plurality of light source signals is applied.

In operation 703, the apparatus for PCR diagnosis may obtain fluorescence power for each of the plurality of code signals for each of the DNA cells based on fluorescence data including a plurality of fluorescence signals received by the receiver from a phosphor attached to each of the plurality of DNAs, to which the plurality of light source signals is applied.

In operation 704, in the apparatus for PCR diagnosis, the receiver may normalize the light source power and the fluorescence power for each of the DNA cells.

The project information related to the present disclosure is as follows.

[Project] 22YR1210
[Project Manager] Cheol HEO
[Contribution] 100
[Assignment Unique Number] None
[Agreement Project] 22YR1200
[Name of National Research Project] Internal R&D Project
[National Research Assignment Name] Development of saliva-based on-site rapid molecular diagnosis technology for new variant viruses
[ETRI Project Name] Development of a saliva-based on-site rapid molecular diagnosis technology for new variant viruses
[Ministry Name] ETRI
[Research Management Institution] ETRI
[Management Organization] Electronics and Telecommunications Research Institute
[Research Period] Jan. 1, 2022 to Dec. 31, 2022

The method according to embodiments may be written in a computer-executable program and may be implemented as various recording media such as magnetic storage media, optical reading media, or digital storage media.

Various techniques described herein may be implemented in digital electronic circuitry, computer hardware, firmware, software, or combinations thereof. The implementations may be achieved as a computer program product, i.e., a computer program tangibly embodied in an information carrier, e.g., in a machine-readable storage device (for example, a computer-readable medium) or in a propagated signal, for processing by, or to control an operation of, a data processing apparatus, e.g., a programmable processor, a computer, or multiple computers. A computer program, such as the computer program(s) described above, may be written in any form of a programming language, including compiled or interpreted languages, and may be deployed in any form, including as a stand-alone program or as a module, a component, a subroutine, or other units suitable for use in a computing environment. A computer program may be deployed to be processed on one computer or multiple computers at one site or distributed across multiple sites and interconnected by a communication network.

Processors suitable for processing of a computer program include, by way of example, both general and special purpose microprocessors, and any one or more processors of any kind of digital computer. Generally, a processor will receive instructions and data from a read-only memory or a random-access memory, or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Examples of information carriers suitable for embodying computer program instructions and data include semiconductor memory devices, e.g., magnetic media such as hard disks, floppy disks, and magnetic tape, optical media such as compact disk read only memory (CD-ROM) or digital video disks (DVDs), magneto-optical media such as floptical disks, read-only memory (ROM), random-access memory (RAM), flash memory, erasable programmable ROM (EPROM), or electrically erasable programmable ROM (EEPROM). The processor and the memory may be supplemented by, or incorporated in special purpose logic circuitry.

In addition, non-transitory computer-readable media may be any available media that may be accessed by a computer and may include both computer storage media and transmission media.

Although the present specification includes details of a plurality of specific embodiments, the details should not be construed as limiting any invention or a scope that can be claimed, but rather should be construed as being descriptions of features that may be peculiar to specific embodiments of specific inventions. Specific features described in the present specification in the context of individual embodiments may be combined and implemented in a single embodiment. On the contrary, various features described in the context of a single embodiment may be implemented in a plurality of embodiments individually or in any appropriate sub-combination. Furthermore, although features may operate in a specific combination and may be initially depicted as being claimed, one or more features of a claimed combination may be excluded from the combination in some cases, and the claimed combination may be changed into a sub-combination or a modification of the sub-combination.

Likewise, although operations are depicted in a specific order in the drawings, it should not be understood that the operations must be performed in the depicted specific order or sequential order or all the shown operations must be performed in order to obtain a preferred result. In specific cases, multitasking and parallel processing may be advantageous. In addition, it should not be understood that the separation of various device components of the aforementioned embodiments is required for all the embodiments, and it should be understood that the aforementioned program components and apparatuses may be integrated into a single software product or packaged into multiple software products.

The embodiments disclosed in the present specification and the drawings are intended merely to present specific embodiments in order to aid in understanding of the disclosure, but are not intended to limit the scope of the disclosure. It will be apparent to those skilled in the art that various modifications based on the technical spirit of the present disclosure, as well as the disclosed embodiments, can be made.

What is claimed is:

1. An apparatus for polymerase chain reaction (PCR) diagnosis, the apparatus comprising:
    a transmitter comprising a multi-wavelength light source for outputting a plurality of light source signals, and configured to apply the plurality of light source signals to a side surface or a rear surface of a PCR chip comprising a plurality of deoxyribonucleic acid (DNA) cells using the multi-wavelength light source, wherein each of the plurality of DNA cells comprises a plurality of DNAs;
    a code generator configured to generate a plurality of code signals corresponding to the plurality of light source signals, respectively, wherein the plurality of code signals is a Walsh code; and
    a receiver configured to receive light source reflection data comprising a plurality of light source reflection signals reflected from each of the DNA cells, to which the plurality of light source signals is applied, obtain light source power for each of the plurality of code signals for each of the DNA cells based on the light source reflection data, receive fluorescence data comprising a plurality of fluorescence signals received from a phosphor attached to each of the plurality of DNAs, to which the plurality of light source signals is applied, obtain fluorescence power for each of the plurality of code signals for each of the DNA cells based on the fluorescence data, and normalize the light source power and the fluorescence power for each of the DNA cells.

2. The apparatus of claim 1, wherein the light source power is obtained for each of the plurality of code signals for each of the DNA cells by a dot product of the plurality of code signals and the light source reflection data comprising the plurality of light source reflection signals reflected from each of the DNA cells in response to the light source signal from each of the DNA cells, to which the plurality of light source signals is applied.

3. The apparatus of claim 1, wherein the fluorescence power is obtained for each of the plurality of code signals for each of the DNA cells by a dot product of the plurality of code signals and the fluorescence data comprising the plurality of fluorescence signals emitted from a phosphor attached to each of the plurality of DNAs, to which the plurality of light source signals is applied.

4. The apparatus of claim 1, wherein the receiver is configured to normalize the light source power and the fluorescence power for each of the plurality of code signals for each of the DNA cells by a ratio of the fluorescence power to the light source power.

5. The apparatus of claim 1,
    wherein the receiver comprises a camera configured to receive the light source reflection data and the fluorescence data, and
    wherein the camera is configured to receive the light source reflection data and the fluorescence data through two optical fibers connected to the receiver.

6. The apparatus of claim 5, wherein the receiver comprises:
- a first filter configured to, for one of the two optical fibers, block the light source reflection data and pass the fluorescence data; and
- a second filter configured to, for the other one of the two optical fibers, attenuate an intensity of the light source reflection data.

7. The apparatus of claim 5,
wherein one of the two optical fibers has an end connected to the receiver, where a first filter configured to block the light source reflection data and pass the fluorescence data is coated, and
wherein the other one of the two optical fibers has an end connected to the receiver, where a second filter configured to attenuate an intensity of the light source reflection data is coated.

8. An apparatus for polymerase chain reaction (PCR) diagnosis, the apparatus comprising:
- a transmitter comprising a multi-wavelength light source for outputting a plurality of light source signals, and configured to apply the plurality of light source signals to each of a plurality of deoxyribonucleic acid (DNA) cells through an optical fiber bundle comprising a plurality of optical fibers connected to an optical splitter, wherein the plurality of DNA cells is included in a PCR chip and each of the plurality of DNA cells comprises a plurality of DNAs;
- a code generator configured to generate a plurality of code signals corresponding to the plurality of light source signals, respectively, wherein the plurality of code signals is a Walsh code; and
- a receiver configured to receive light source reflection data comprising a plurality of light source reflection signals received through the optical fiber bundle from each of the DNA cells, to which the plurality of light source signals is applied, obtain light source power for each of the plurality of code signals for each of the DNA cells based on the light source reflection data, receive fluorescence data comprising a plurality of fluorescence signals received through the optical fiber bundle from a phosphor attached to each of the plurality of DNAs, to which the plurality of light source signals is applied, obtain fluorescence power for each of the plurality of code signals for each of the DNA cells based on the fluorescence data, and normalize the light source power and the fluorescence power for each of the DNA cells.

9. The apparatus of claim 8, wherein the light source power is obtained for each of the plurality of code signals for each of the DNA cells by a dot product of the plurality of code signals and the light source reflection data comprising the plurality of light source reflection signals reflected from each of the DNA cells in response to the light source signal from each of the DNA cells, to which the plurality of light source signals is applied.

10. The apparatus of claim 8, wherein the fluorescence power is obtained for each of the plurality of code signals for each of the DNA cells by a dot product of the plurality of code signals and the fluorescence data comprising the plurality of fluorescence signals emitted from a phosphor attached to each of the plurality of DNAs, to which the plurality of light source signals is applied.

11. The apparatus of claim 8, wherein the receiver is configured to normalize the light source power and the fluorescence power for each of the plurality of code signals for each of the DNA cells by a ratio of the fluorescence power to the light source power.

12. The apparatus of claim 8, wherein the optical fiber bundle comprises an optical fiber for applying the plurality of light source signals, an optical fiber for receiving the light source reflection data comprising the plurality of light source reflection signals, and an optical fiber for receiving the fluorescence data comprising the plurality of fluorescence signals.

13. The apparatus of claim 12,
wherein a filter for attenuating an intensity of the light source reflection data is coated on one end of the optical fiber for receiving the light source reflection data, and
wherein a filter for blocking the light source reflection data and passing only the fluorescence data is coated on one end of the optical fiber for receiving the fluorescence data.

14. An operating method performed by an apparatus, the method comprising:
- applying, using a transmitter comprising a multi-wavelength light source for outputting a plurality of light source signals, the plurality of light source signals to a side surface or a rear surface of a polymerase chain reaction (PCR) chip comprising a plurality of deoxyribonucleic acid (DNA) cells, wherein each of the plurality of DNA cells comprises a plurality of DNAs and the plurality of light source signals corresponds to a plurality of code signals generated by a code generator, respectively;
- obtaining light source power for each of the plurality of code signals for each of the DNA cells based on light source reflection data comprising a plurality of light source reflection signals received by a receiver from each of the DNA cells, to which the plurality of light source signals is applied;
- obtaining fluorescence power for each of the plurality of code signals for each of the DNA cells based on fluorescence data comprising a plurality of fluorescence signals received by the receiver from a phosphor attached to each of the plurality of DNAs, to which the plurality of light source signals is applied; and
- normalizing the light source power and the fluorescence power for each of the DNA cells by the receiver.

15. The method of claim 14, wherein the obtaining of the light source power for each of the plurality of code signals comprises:
- obtaining the light source power for each of the plurality of code signals for each of the DNA cells by a dot product of the plurality of code signals and the light source reflection data comprising the plurality of light source reflection signals reflected from each of the DNA cells in response to the light source signal from each of the DNA cells, to which the plurality of light source signals is applied.

16. The method of claim 14, wherein the obtaining of the fluorescence power for each of the plurality of code signals comprises:
- obtaining the fluorescence power for each of the plurality of code signals for each of the DNA cells by a dot product of the plurality of code signals and the fluorescence data comprising the plurality of fluorescence signals emitted from a phosphor attached to each of the plurality of DNAs, to which the plurality of light source signals is applied.

17. The method of claim 14, wherein the normalizing comprises:

normalizing the light source power and the fluorescence power for each of the plurality of code signals for each of the DNA cells by a ratio of the fluorescence power to the light source power.

18. The method of claim 14,
wherein the receiver comprises a camera configured to receive the light source reflection data and the fluorescence data, and
wherein the camera is configured to receive the light source reflection data and the fluorescence data through two optical fibers connected to the receiver.

19. The method of claim 18, wherein the receiver comprises:
a first filter configured to, for one of the two optical fibers, block the light source reflection data and pass the fluorescence data; and
a second filter configured to, for the other one of the two optical fibers, attenuate an intensity of the light source reflection data.

20. The method of claim 18,
wherein one of the two optical fibers has an end connected to the receiver, where a first filter configured to block the light source reflection data and pass the fluorescence data is coated, and
wherein the other one of the two optical fibers has an end connected to the receiver, where a second filter configured to attenuate an intensity of the light source reflection data is coated.

* * * * *